(12) United States Patent
Bean et al.

(10) Patent No.: US 9,333,371 B2
(45) Date of Patent: May 10, 2016

(54) VARIABLE INTENSITY LASER TREATMENTS OF THE SKIN

(71) Applicant: SemiNex Corporation, Peabody, MA (US)

(72) Inventors: David M. Bean, Middleton, MA (US); Matthew Hamerstrom, Salem, MA (US); Alyssa Bean, Topsfield, MA (US)

(73) Assignee: SemiNex Corporation, Peabody, MA (US)

( * ) Notice: Subject to any disclaimer, the term of this patent is extended or adjusted under 35 U.S.C. 154(b) by 0 days.

(21) Appl. No.: 14/065,640

(22) Filed: Oct. 29, 2013

(65) Prior Publication Data
US 2014/0121631 A1    May 1, 2014

Related U.S. Application Data

(60) Provisional application No. 61/721,331, filed on Nov. 1, 2012.

(51) Int. Cl.
*A61N 5/06* (2006.01)
*A61N 7/02* (2006.01)
(Continued)

(52) U.S. Cl.
CPC ............ *A61N 5/0616* (2013.01); *A61B 18/203* (2013.01); *A61N 7/02* (2013.01);
(Continued)

(58) Field of Classification Search
CPC ........... A61N 5/06–5/0625; A61N 2005/0644; A61N 2005/0659; A61N 2005/067; A61B 18/203
USPC .................... 607/88–91, 96, 100–102; 606/9; 128/898
See application file for complete search history.

(56) References Cited

U.S. PATENT DOCUMENTS 4,950,268 A     8/1990  Rink
5,269,778 A    12/1993  Rink et al.
(Continued)

FOREIGN PATENT DOCUMENTS

WO        2012106678 A1    8/2012

OTHER PUBLICATIONS

International Search Report and Written Opinion of the International Searching Authority mailed Mar. 25, 2014 from counterpart International Application No. PCT/US2013/067184, filed Oct. 29, 2013.
(Continued)

*Primary Examiner* — Lynsey Crandall
*Assistant Examiner* — Nathan J Jenness
(74) *Attorney, Agent, or Firm* — HoustonHogle, LLP

(57) ABSTRACT

A method for providing localized heating of the dermal layers of skin of a patient, using energy in the form of a group of pulses having defined parameters in a controlled manner. This method preferably uses an optical delivery system to deliver pulsed energy to a specific spot of skin so that targeted layers of the affected skin are heated to a desired temperature range. The temperature range is optimally selected to maximize treatment efficacy while minimizing pain to the patient. Example applications include reducing wrinkles, acne, hair, scar tissue, warts, and promoting wound healing. In this method, the temperature of the selected locus rises quickly to the desired temperature range, then is maintained within a controlled range with a relatively flat temperature profile. The method maintains the temperature by controlling one or more of a pulse energy intensity, pulse width, and pulse frequency or time delay between pulses.

14 Claims, 19 Drawing Sheets

(51) Int. Cl.
  *A61B 18/20* (2006.01)
  *A61B 18/00* (2006.01)
  *A61B 19/00* (2006.01)
  *A61N 5/067* (2006.01)
  *A61B 17/00* (2006.01)

(52) U.S. Cl.
  CPC .......... *A61B2017/00172* (2013.01); *A61B 2018/0047* (2013.01); *A61B 2018/00476* (2013.01); *A61B 2018/00642* (2013.01); *A61B 2018/00702* (2013.01); *A61B 2018/00791* (2013.01); *A61B 2018/202* (2013.01); *A61B 2019/465* (2013.01); *A61N 5/0624* (2013.01); *A61N 5/0625* (2013.01); *A61N 2005/067* (2013.01); *A61N 2005/0644* (2013.01); *A61N 2005/0659* (2013.01)

(56) References Cited

U.S. PATENT DOCUMENTS

| | | | |
|---|---|---|---|
| 5,689,520 | A | 11/1997 | Hoang |
| 5,836,999 | A | 11/1998 | Eckhouse et al. |
| 6,165,171 | A | 12/2000 | Tobinick |
| 6,168,589 | B1 | 1/2001 | Tobinick |
| 6,514,278 | B1 * | 2/2003 | Hibst et al. .............. 607/89 |
| 6,595,985 | B1 | 7/2003 | Tobinick |
| 6,998,567 | B2 | 2/2006 | Yeik |
| 7,251,531 | B2 * | 7/2007 | Mosher et al. .............. 607/102 |
| 7,413,572 | B2 | 8/2008 | Eimerl et al. |
| 7,856,985 | B2 | 12/2010 | Mirkov et al. |
| 8,029,553 | B2 | 10/2011 | Nemenov |
| 8,888,830 | B2 | 11/2014 | Dunleavy et al. |
| 8,974,443 | B2 | 3/2015 | Dunleavy et al. |
| 2004/0133251 | A1 * | 7/2004 | Altshuler et al. .............. 607/88 |
| 2005/0107852 | A1 * | 5/2005 | Levernier et al. .............. 607/89 |
| 2005/0171581 | A1 * | 8/2005 | Connors et al. .............. 607/88 |
| 2007/0213696 | A1 * | 9/2007 | Altshuler et al. .............. 606/9 |
| 2008/0058783 | A1 * | 3/2008 | Altshuler et al. .............. 606/9 |
| 2008/0172045 | A1 | 7/2008 | Shanks et al. |
| 2009/0012585 | A1 * | 1/2009 | Karni et al. .............. 607/88 |
| 2009/0254068 | A1 * | 10/2009 | Karni et al. .............. 606/3 |
| 2011/0122905 | A1 | 5/2011 | Bean et al. |
| 2011/0152847 | A1 | 6/2011 | Mirkov et al. |
| 2012/0197357 | A1 | 8/2012 | Dewey et al. |

OTHER PUBLICATIONS

Dams, S., "The Effect of Heat Shocks in Skin Rejuvenation," Koninklijke Philips Electronics N.V., 2010, 129 pages.
International Preliminary Report on Patentability, mailed May 14, 2015, from counterpart International Application No. PCT/US2013/067184, filed Oct. 29, 2013.

* cited by examiner

VARIABLE INTENSITY LASER TREATMENTS OF THE SKIN

This application claims the benefit under 35 USC 119(e) of U.S. Provisional Application No. 61/721,331, filed on Nov. 1, 2012, which is incorporated herein by reference in its entirety.

BACKGROUND OF THE INVENTION

Lasers for treating skin ailments, hair removal, and other dermal procedures were first introduced in the 1990s. Laser wavelengths are absorbed in the skin or in other tissues to provide limited localized damage, which causes the body to respond in a desired manner. One example includes lasers that provide localized damage to hair follicle cells, which causes permanent hair removal. Another example includes lasers that provide localized damage to the dermal layers, which causes wrinkle or acne reduction in the skin.

A schematic drawing of the outer layers of the skin is shown in FIG. 5. The outer layer of the skin, the epidermis, is the familiar outer layer of skin cells. Below the epidermis is the dermis, which comprises living epidermal cells, local vascularization, and additional structures including hair follicles, collagen, elastin and secretory cells. The dermis is the primary target site for treatment of the skin for lasting or permanent changes. It is most desirable to leave the epidermis unaffected and undamaged during a treatment procedure. To achieve this, the epidermis can be intentionally cooled during such treatment procedure, or the procedure can be tailored to avoid any significant heat to the epidermis. This approach will minimize pain and recovery times and ideally with no visible scarring, redness, or side effects.

There are a number of past and current examples of laser treatments for skin. For example, U.S. Pat. No. 8,029,553 to Nemenov describes a laser system and process using a near-IR laser at 980 nanometers (nm) to produce controlled variable heating and stimulation of single nerve fibers in tissue, while avoiding nerve damage. U.S. Pat. No. 7,856,985 to Mirkov et al. and U.S. Published Patent Application No. 2011/0152847 by Mirkov et al. describe remodeling of skin using high intensity laser pulses to shrink skin collagen, and using low intensity radiation to stimulate fibroblasts for renewed collagen production. U.S. Pat. No. 7,413,572 to Eimerl et al. describes irradiating tissue with a sequence of optical pulses. Then, tissue properties are measured and used to vary the intensity of irradiation to produce desired results. U.S. Pat. No. 6,998,567 to Yeik describes the creation and delivery of laser pulse trains.

U.S. Pat. No. 6,595,985 to Tobinick uses laser pulses to remove hair follicles and cooling the epidermis with fluid spray to prevent skin damage. U.S. Pat. Nos. 6,165,171 and 6,168,589 to Tobinick describe two lasers of different wavelengths to remove hair follicles. U.S. Pat. No. 5,836,999 to Eckhouse et al. discloses treatment of psoriasis with non-laser optical energy. In this example, pulse number and width are selected to control penetration, and cooling may be supplied to the skin surface. U.S. Pat. No. 5,689,520 to Hoang describes a method and apparatus for obtaining a variable output waveform in surgery.

U.S. Pat. No. 5,269,778 to Rink et al. and U.S. Pat. No. 4,950,268 to Rink use pulses for vaporization of tissue at a tissue site producing localized plasma.

SUMMARY OF THE INVENTION

The attributes of optical power, pulse width (also referred to as pulse duration), time delay between pulses, and total number of pulses dictate the total time and total energy during a treatment cycle. The same treatment cycle can be represented identically with the terms optical power, pulse frequency, duty cycle, and total treatment time. For example, the same pulse treatment can be expressed by either using pulse width and time delay between cycles or duty cycle and pulse frequency. Thus, these combinations of terms may be interchangeable as it relates to the following explanations of methods of treatment. Optical power (also expressed as energy intensity, or laser power if a laser is used to generate the optical energy) is typically varied by setting the current that flows through the light emitting element such as a laser diode or light-emitting diodes (LED).

Typically, for a given treatment, the system user will fix the four attributes listed above (laser power, pulse width, time delay between pulses, and total number of pulses) through the system controls interface. Once these settings are fixed, the laser will be turned on and the patient will be treated with the sequence of pulses as determined by these settings. Such an approach delivers a consistent stream of energy into the patient as illustrated in FIG. 7. This generates a thermal profile in the skin which rises linearly then decreases linearly once the laser power is removed. However, this linear power implementation and linear temperature profile is not ideal for treating skin ailments.

The number of pulses or the total time the laser is in operation is typically fixed for a given treatment setting. Typically, all pulses are identical in pulse width and in time delay between pulses. The number of pulses is controlled by a computer or electrical system to repeat the pulsing sequence until the defined number of pulses is reached. The lasers are pulsed to allow for the human tissue to absorb the energy without an extreme energy spike within the tissue which can cause burning or similar unwanted outcomes. The time delays between pulses allow the tissue to relax and the energy to be absorbed and spread within the tissue before the next pulse introduces additional energy into the tissue.

A more ideal treatment for skin disease, skin ailments, skin wrinkles, and the like is to raise the temperature of the exact depth and area of the skin where a thermal response is desired to a relatively exacting temperature that is known to promote a desirable cellular response. Then, the temperature is maintained until the promoted response has sufficiently taken place. To achieve the desired temperature profile, the laser system must operate in a non-linear fashion. For example, the laser may initially drive at a high fluence (high rate of energy transfer) into the skin until the desired temperature is reached, lower its fluence to allow the energy to evenly distribute in the targeted skin, and then finally modify its fluence to maintain this desired dermal temperature.

Current laser treatment for skin wrinkles uses a set of repetitive laser pulses, as illustrated in FIG. 7, to raise the temperature of the skin to temperatures of greater than 60 degrees Celsius (C) in small fractional areas of the skin, which typically represents less than 10 percent of the entire skin area. The skin cells affected by this laser energy are damaged or destroyed, and in response, send out heat shock protein signals and signals causing the body to fully regenerate these destroyed skin cells. This method relies on cells adjacent to the damaged cells for help to rebuild the skin quickly. This treatment is typically repeated many times using daily or weekly treatment frequency. This not only randomizes the locations of the skin damaged by the treatment, but also provides the ability to treat all skin over time. Over time, most or all of the skin is regenerated. This method has several drawbacks such as causing pain to the patient, redness of the skin, and high laser system costs.

An alternate method for skin wrinkle reduction was published in 2010 in the Reference Heat-Shock Protein Study, titled "The effect of heat shocks in skin rejuvenation," by Susanne Dams. In this study, an alternate method is evaluated that raises the skin temperature to only 45 degrees C. According to Dams, the lower temperature stimulates heat-shock protein formation while also maintaining an energy level and temperature within the skin that is typically below the pain threshold for most patients. Studies have shown that the temperature of the skin dermis is the salient factor in promoting the desired medical effect of interest. As a result, it is desirable to reach the needed temperature quickly and then maintain that specific temperature for a period of time. The time at which the skin is maintained at that given temperature often correlates with the effectiveness of treatment.

In the case of wrinkle reduction within skin, it is desirable to raise the temperature of the dermal layer of the skin above 39 degrees C. Doing so triggers the dermal cells to release heat-shock proteins (HSP) to promote collagen formation, new cell formation, and collagen reconfiguration, which may reduce skin wrinkles At a temperature of 45 degrees C., humans begin to feel pain in the dermis. Thus, an ideal way to stimulate HSP and other cell benefits without incurring pain is to raise the dermal temperature between 39 degrees C. and 45 degrees C. while also maintaining this temperature for a fixed period of time. Though the period of time depends on the specific treatment, it is ideally greater than 0.5 seconds.

At these temperatures, the dermal cells release heat-shock proteins, which promote collagen remodeling, new collagen growth and/or elastin formation. Collagen remodeling is a relaxing of the collagen, which allows tangled and twisted collagen to reform into flat linear collagen strands. This promotes soft, smooth, and healthy looking skin. The flattening of the existing collagen is combined with the addition of new collagen, as promoted by the introduction of the heat-shock protein, to reduce or eliminate fine wrinkles in human skin. The aforementioned Dams study noted that increasing temperature higher than 45 degrees C. in the skin's dermal layer did not have a significant additional benefit. Thus, raising temperature in the dermis to between 39 degrees C. and 45 degrees C. is highly preferential, as it maximizes effectiveness with minimal energy (high efficiency), while also minimizing pain and other skin side effects such as redness.

The ideal laser treatment approach involves raising the dermal temperature to between 39 degrees C. and 45 degrees C. and maintaining this temperature for a time such that when the laser is removed, the temperature continues to remain at the elevated temperature for much longer than the time of the treatment itself. Ideally, the laser treatment time is between 0.2 and 1.5 seconds and causes a temperature elevation within the range of 39 degrees C. to 45 degrees C. in the skin that lasts for 1 second or longer.

An improved method of laser treatment is needed to more precisely apply energy into the skin. The preciseness of the energy application of the improved method will allow the skin to reach a relatively fixed temperature level while avoiding temperature spikes, and will prolong the treatment time at the desired temperature to maximize efficacy of the dermal treatment.

A new method of laser treatment has been developed to raise the temperature in desired portions of a tissue to a desired temperature level and to maintain this temperature for a desired amount of time. This method provides the following advantages: 1) increased efficacy, 2) increased safety, with burning of the skin eliminated, 3) increased speed of treatment, 4) more localized heating of the skin to avoid collateral damage to areas not of interest, 5) increased usefulness for treatment of all skin types and colors, 6) increased comfort and pain avoidance in the treatment process.

This invention relates to an improved method employing a laser apparatus for generating heat in the dermal layers of the skin. Specifically, the invention relates to sending out a series of laser pulses to a targeted area of skin. The pulses are pre-defined to vary in pulse intensity, pulse width, and delay between pulses. This enables the temperature in the dermal layer to rise quickly to a desired temperature range, then level off and stay within the temperature range without becoming significantly hotter or colder. This provides an improved cellular response without overheating portions of the skin, which avoids collateral damage and pain to the patient's skin.

In general, according to one aspect, the invention features a method for providing localized heating of target spots of skin of a patient. This method includes applying laser energy to the target spots in an affected area of skin such that the skin is heated so that a temperature of each target spot rises quickly to a desired heating temperature range. Also, this method includes maintaining the temperature in the target spots within the desired heating temperature range by controlling, in pulses or continuously, at least one beam parameter including an energy intensity, a pulse width, or a time delay between pulses. One or more of the beam parameters change throughout the application of the laser energy.

The energy is preferably delivered to the target spot based on pulsed beam parameters. The pulsed beam parameters are selected from the pulse width, the time delay between pulses, and the pulse energy intensity (or equivalently duty cycle and pulse energy intensity). Then, one or more pulsed beam parameters are initially set to raise the temperature in the skin, then as the heating progresses the parameters are changed so as to maintain the desired temperature range in the skin.

In one example the energy is delivered to the target spot as a continuous energy beam, where time delay between pulses is zero (there are no separate pules) and only the energy intensity varies with time during the heating.

In one example, the pulses are applied in a first group of pulses to quickly heat the skin to a target temperature, and thereafter the pulses are applied in a second group of pulses to decrease a rate of temperature increase in the target, followed by a third group of pulses to maintain the temperature of the target for a defined period. In another example, the second group of pulses provides less energy/time than the first group of pulses and greater than the third group of pulses. Preferably, a group of pulses after the initial group of pulses provides less energy/time than the first group of pulses and less than a subsequent group of pulses.

According to another example, an interval between pulses increases over time to maintain a tissue temperature in the desired heating temperature range during treatment. The pulses are of variable width and the width of the pulses decreases over time to maintain a tissue temperature in the desired heating temperature range during treatment.

Preferably, the energy intensity varies over time to maintain a tissue temperature in the desired heating temperature range during treatment. The treatment can be utilized to reduce any or all of the following: skin wrinkles, acne, hair, skin discoloration such as age spots, bacterial infections, viral infections, fungal infections, scar tissue or appearance thereof, cellulite, warts, or wound infection.

In general, according to another aspect, the maintained temperature of the method is greater than about 39 degrees Celsius. Preferably, the maintained temperature is greater than about 39 degrees Celsius and less than about 45 degrees Celsius. The energy is typically provided by a laser source, ultrasound or a radio-frequency (RF) source. Preferably, the energy conveyed maintains a dermal temperature of the target spots between about 39 degrees Celsius and about 45 degrees Celsius for greater than about 0.5 seconds.

In one implementation, a safety sensor near an aperture detects a contact or near-contact with the skin, and the method includes only emitting energy while the safety sensor continues to detect contact or near-contact with the skin.

In another example, a laser device that forms the method is connected by a wire or through wireless communications to another device such as a computer to complete one or more operations to the laser device, the operations including updating device software, downloading device data, and charging device battery. Preferably, once the laser device is connected to another device, the laser device automatically launches a program to begin data communications between the devices.

Preferably, the laser device uses an optical wavelength between 1380 nm and 1570 nm. The laser device can be utilized for promoting the healing of wounds, and for promoting vaccine transportation throughout the patient.

In general according to another aspect, the invention features a handheld laser system for providing localized heating of target spots of skin for treating a patient. The system comprises a laser engine for generating light that is applied to the target spots of skin and a controller that drives the laser engine to generate light to maintain the temperature in the target spots within the desired heating temperature range by controlling, in pulses or continuously, at least one beam parameter of the laser engine including an energy intensity, pulse width, or a time delay between pulses, such that one or more of the beam parameters change throughout the application of the energy.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
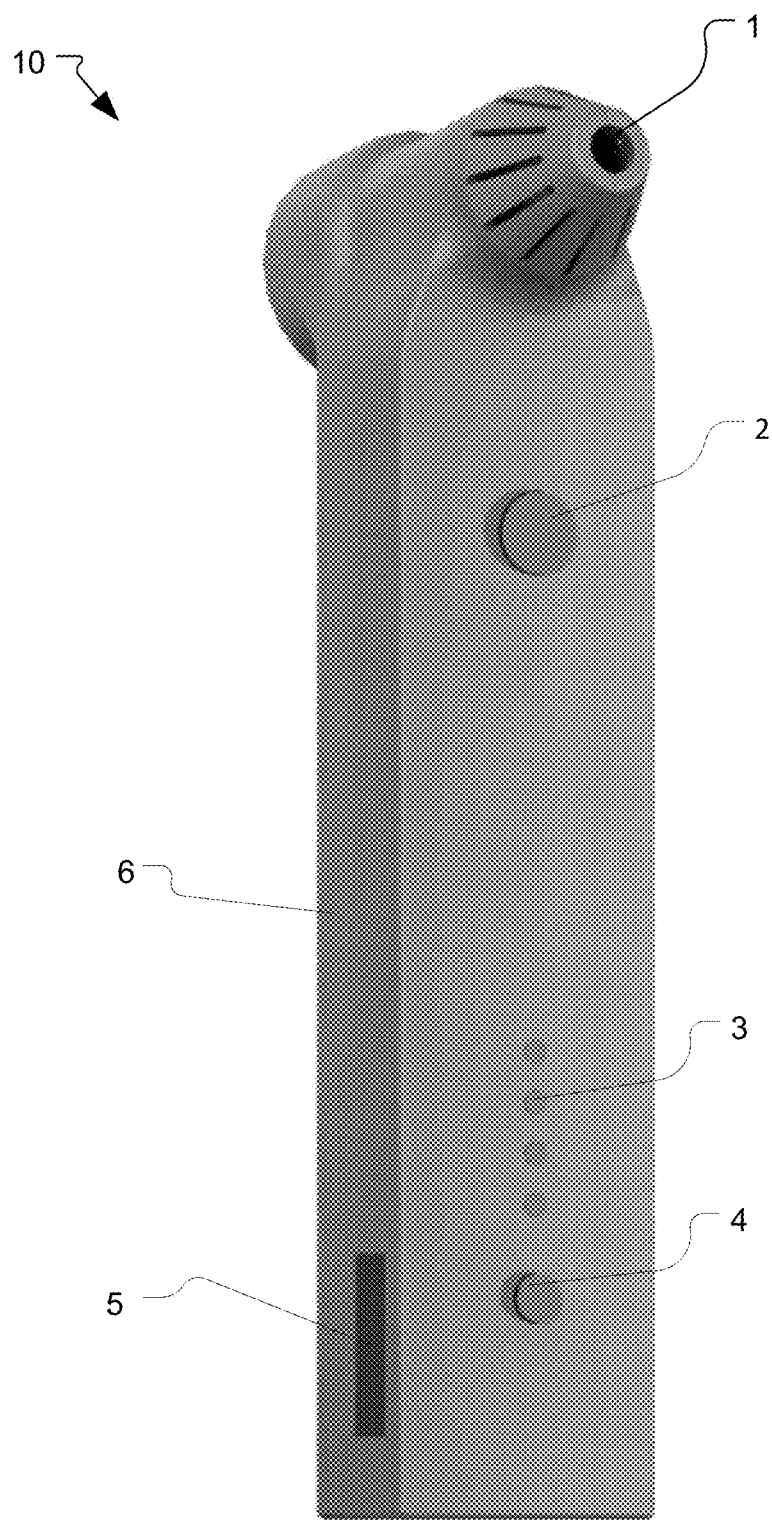
FIG. 1 is a perspective view of a handheld laser system.

FIG. 1 is a simplified handheld laser system 10 that performs the method for providing localized heating of target spots of skin for treating a patient. The system 10 is utilized for treating skin tissue and selected dermatological conditions. Such conditions include acne, skin wrinkles, hair removal, skin discoloration such as age spots, and bacterial, viral, and, fungal infections. In addition, the system 10 reduces scar tissue or its appearance thereof, reduces cellulite and warts, promotes wound healing and disinfection, and promotes the transportation of vaccines throughout the body of the patient.

The system 10 includes an aperture 1 where light is emitted from the device 10, initiation button 2 to initiate the laser treatment sequence, and indicator lighting 3 to notify operator of system status and operating program. The system 10 also includes power button 4 for selecting the power level and/or program sequence, port 5 to connect the device 10 to power the unit and/or to charge the battery and/or communicate with other devices, and handle 6 to encase the system 10 and provide an ergonomic way to handle the system 10 in a human hand.

Port 5 can also be used to connect the device 10 to another device such as a computer. A computer communicates with the system 10 to update the program(s) or download data to the system 10, or communicate with the system over the internet, in examples. The laser system 10 in FIG. 1 is compact and useful for such applications as portable laser operations at home, while traveling away from home, in a doctor's office, or places where medical professionals can operate.

Figure 2:
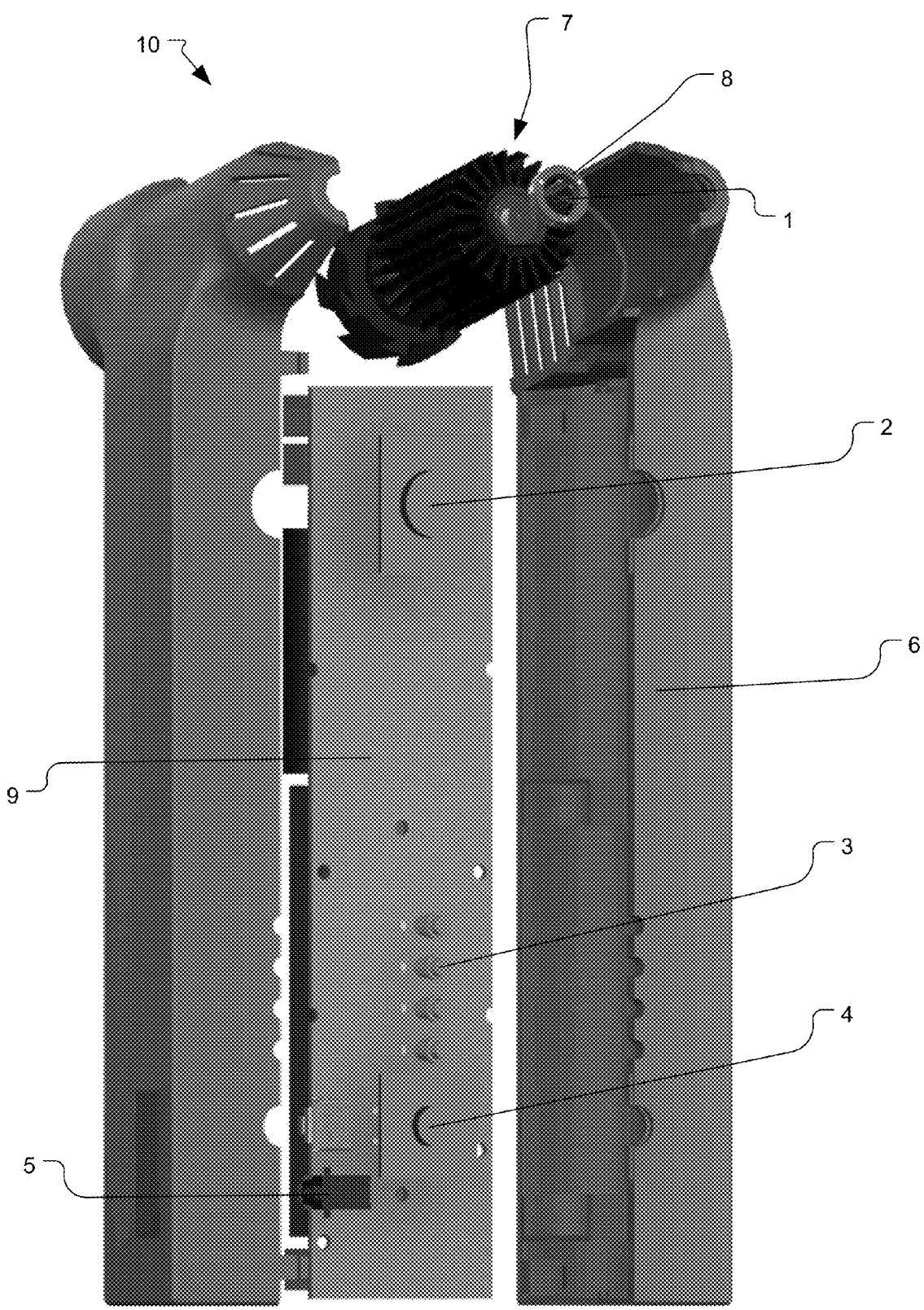
FIG. 2 is an exploded view of the handheld laser system from FIG. 1.

FIG. 2 shows additional details of the laser system 10 in a disassembled (exploded) manner. It shows how the laser system 10 includes a light emitting device or laser engine 7 which has lens(es) and/or fiber optics and a heat dissipation element. In one example, device 7 is constructed as described in U.S. Pat. Appl. Pub. No. US 2011/0122905A1, Pub. Date May 26, 2011, by D. Bean and J. Callahan, which is incorporated herein by this reference in its entirety. This laser system 10 also includes a safety sensor 8 which can determine if the light aperture 1 is in relatively full contact with the skin.

The laser system 10 also includes an internal control board 9 which can include a controller such as a microprocessor(s), capacitors, battery charge circuits, memory, and data communication chips, all of which controls and powers the light emitting device 7 and receives inputs from the initiation button 2, power button 4, and port 5. In this example, the light emitting device 7 includes a fan for convection cooling of the light emitting device. The fan blows air toward the skin through an aperture 1 or pulls air in the other direction away from aperture 1. Air traveling through the aperture 1 driven by the fan is necessary to cool the light emitting device in 7 and may act to cool or heat the surface of the skin directly outside of aperture 1 as a secondary function.

In general, the controller of the of the control board 9 drives the laser engine 7 to generate light to maintain the temperature in the target spots within the desired heating temperature range by controlling, in pulses or continuously, at least one beam parameter of the laser engine 7 including an energy intensity, pulse width, or a time delay between pulses, such that one or more of the beam parameters change throughout the application of the energy.

Figure 3:
FIG. 3 is a perspective view showing how the handheld laser system is held prior to pressing a laser against skin for treatment.

FIG. 3 shows how the handheld laser system 10 can be oriented in a user's hand. This configuration allows for a comfortable and ergonomic grip of the handle with the thumb naturally resting on the initiation button 2.

Figure 4:
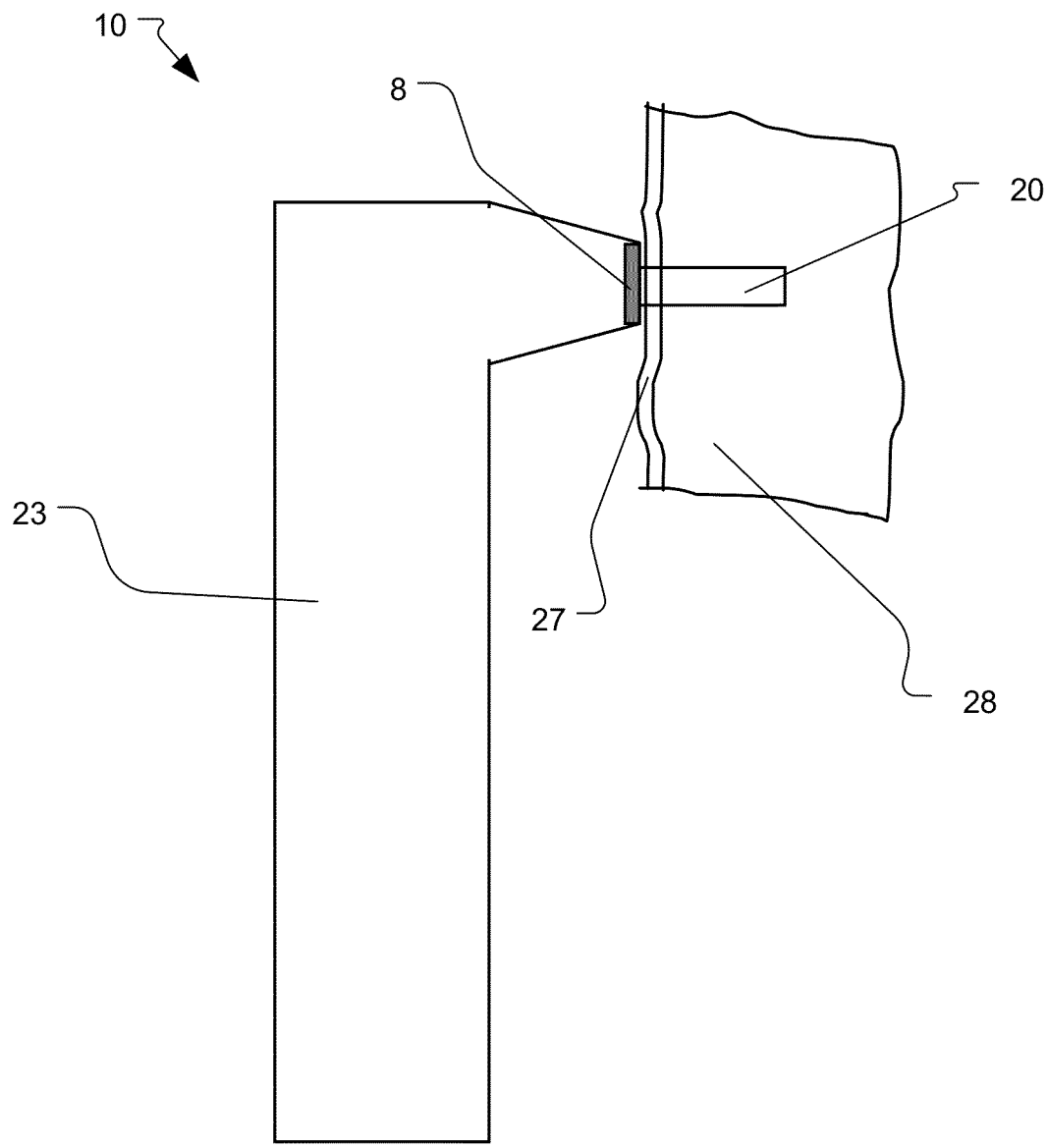
FIG. 4 is a schematic cross-sectional view of the handheld laser system during treatment as it is engaged directly onto the skin.

FIG. 4 shows a basic schematic of the handheld laser system 10 as it is pressed against the outer skin (epidermis) 27 of a patient. The contact configuration in FIG. 4 is used to press the device 23 against the skin 28 such that the contact safety sensor 8 senses that the device 23 is in good contact or close proximity with the epidermis 27 part of the skin 28. In one example, the safety sensor 8 is be made up of multiple sensors each determining if skin is in contact around the circumference of the aperture 1. It is preferable to have multiple sensor reading heads within the safety sensor 8, such that each sensor head is about 120 degrees from each other around the perimeter of the aperture 1.

Also, the controller of the control board 9 preferably ensures that all of the sensor reading heads are touching the skin 28 to ensure there are no significant gaps in contact where emitting light could leak out from the desired treatment area. Reference 20 represents the light being emitted into the skin 28 from the laser system 10 and penetrating through the epidermis 27 into the dermis 28 or skin layer. By choosing the appropriate wavelength of the light emitter 7 within the system 10, the light will be absorbed at depths within the dermal layers according to the absorption characteristics of the wavelength. Wavelengths between 1380 nm and 1570 nm are well suited to be absorbed in the dermis and reduce or eliminate acne, skin wrinkles, and many bacterial/viral infections in the skin. Such penetration of laser energy between 100 microns and 800 microns is desirable for these applications.

Figure 5:
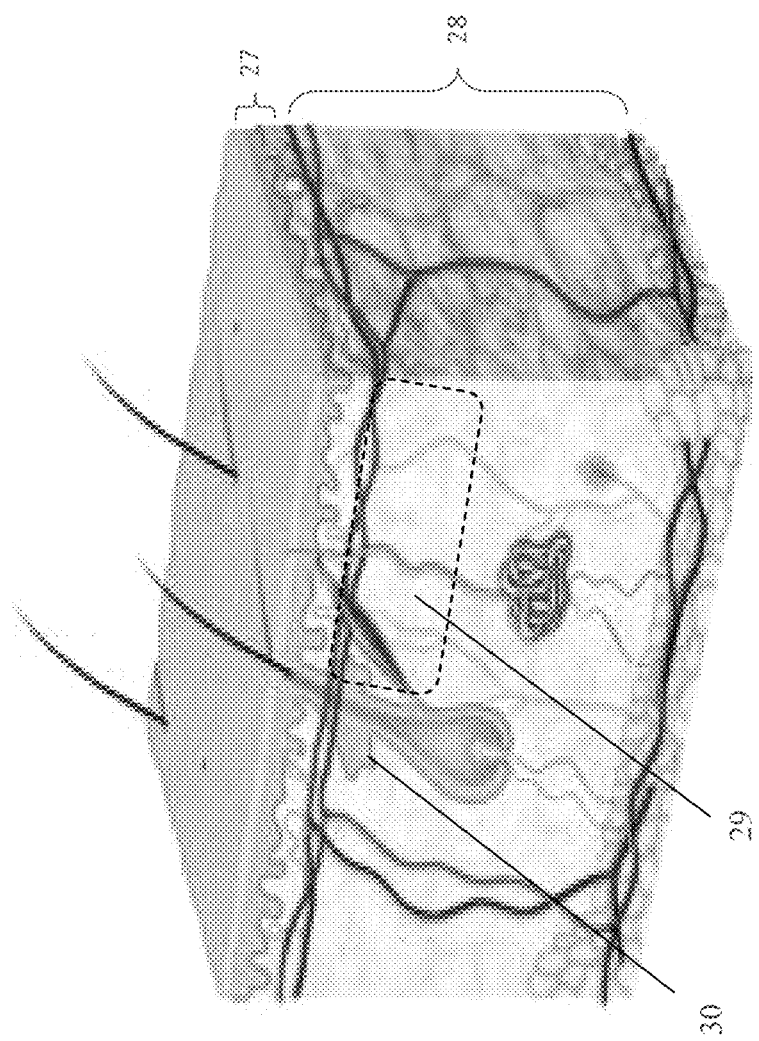
FIG. 5 is a perspective view of the structures of the skin.

FIG. 5 shows the skin structure of a patient that includes the epidermis 27, collagen layers 29, sebaceous gland 30, and dermis 28. The treatment provided by the system 10 enacts beneficial, long-lasting or permanent changes to the dermis 28 without damaging or affecting the epidermis 27.

Figure 6:
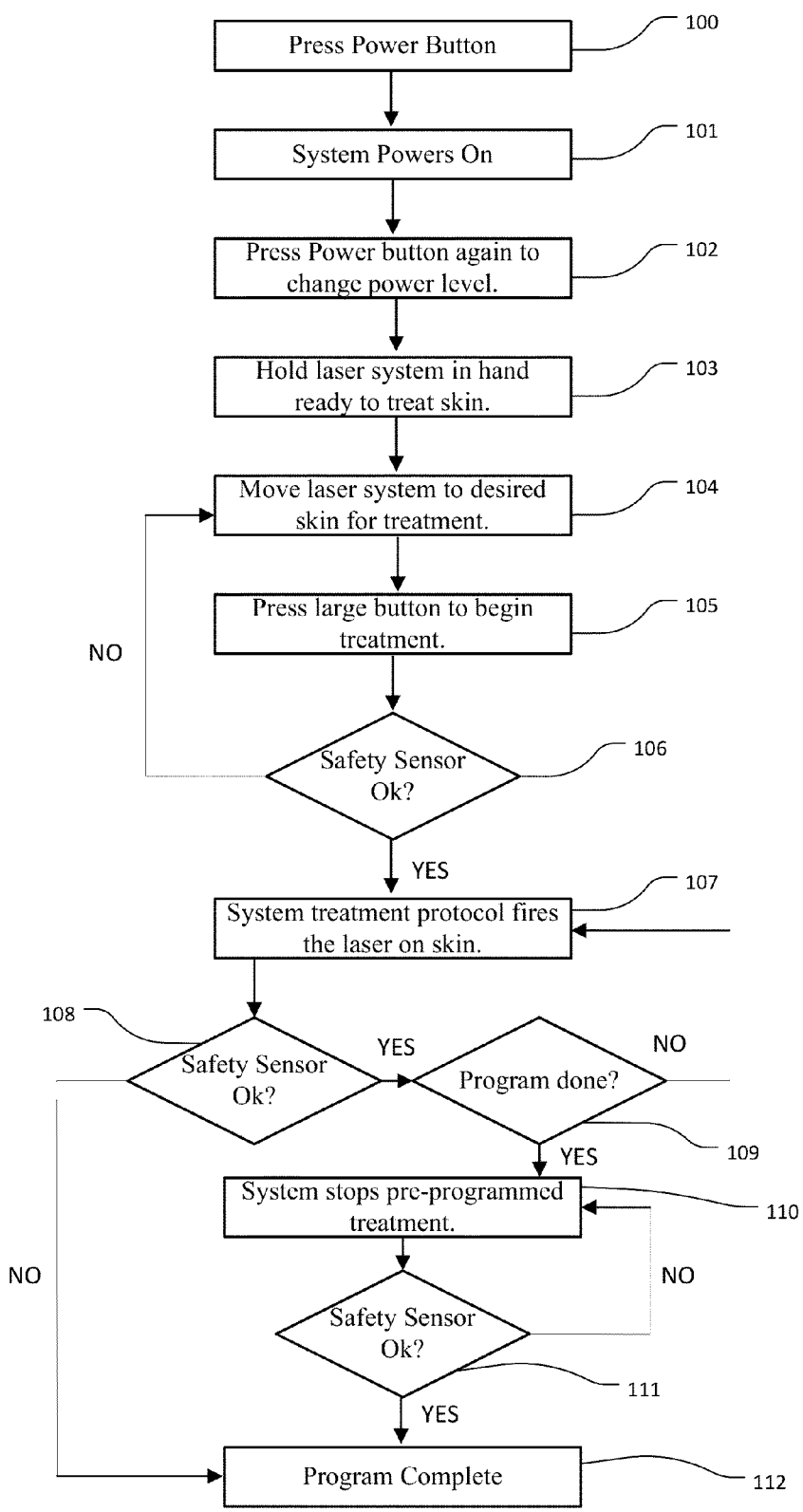
FIG. 6 is a flowchart illustrating the handheld laser system operation.
Figure 7:
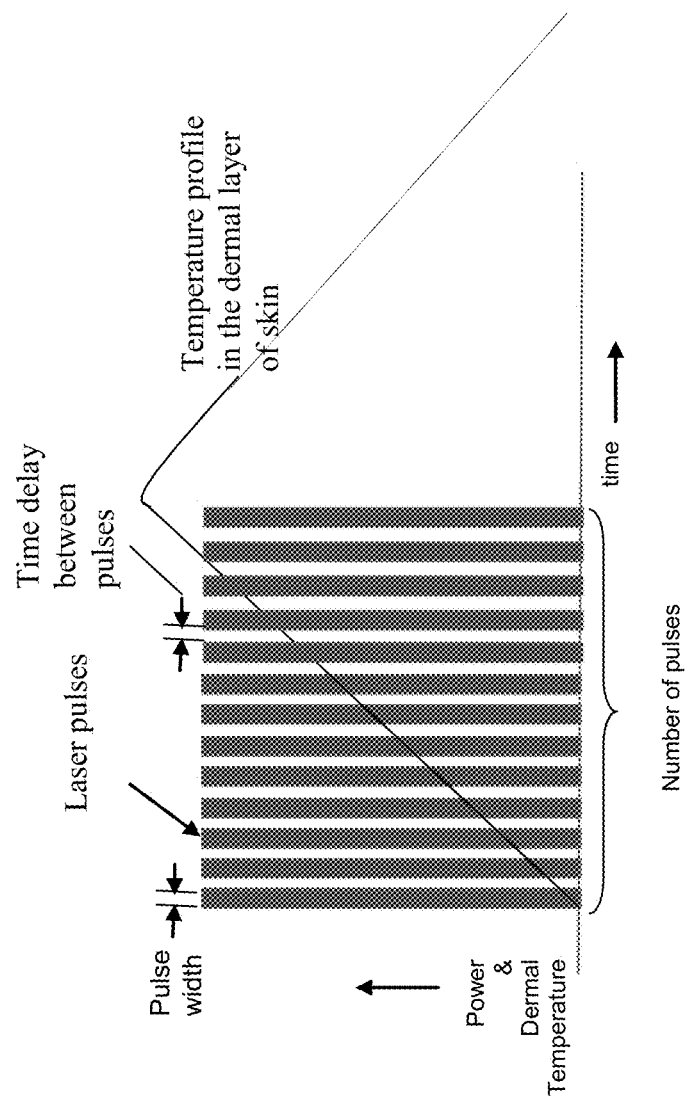
FIG. 7 is a graphical view of a simple pulse pattern in which all pulses are the same in pulse intensity, pulse duration and time between pulses, providing a temperature profile that peaks and then declines.

FIG. 6 is a flow chart outlining an example of how to use the laser system 10 for administering laser treatments using the handheld laser device 23 (system 10). In more detail, the power button 4 is pressed to energize the system 10 in step 100. Once the power button 4 is engaged in step 100, the system 10 is programmed to launch into step 101 and provide an audio signal, such as a jingle from a speaker or buzzer element on the control board 9. Then, the indicator lighting 3 such as LEDs light up to indicate that the power is on and indicate which preset laser program/power level the device is set to perform at.

Upon initial power up in step 101, the lowest power level is automatically set by for the user by the system control program of the controller of the control board 9. In step 102, the user may now press the power button 4 such as a power/program select button 4 to change the power/program that will be used once the laser is in operation. The user may continue to press the power button 4 to cycle through power levels such as low to medium to high, back to low, and so forth. Each time the power button 4 is pressed, the LED lights of the indicator lighting 3 change configurations to represent the power level selection. Low power is represented by the second LED from the bottom of the laser device 23, medium power is represented by the third LED from the bottom of the laser device 23, and high power is represented by the top LED of the laser device 23. The bottom LED of the laser device 23 is used to represent that the power is on.

There can be more than 3 power levels used within the laser system 10. In one example, 5 power levels are used. This enables the user to select the best level to meet their needs during use and ideally avoid any physical discomfort to the user. The system 10 may be reprogrammed for 4 power levels by using all four LEDs 3 as power levels 1 through 4 and omit a power-on light which can be assumed by seeing one of the power level lights on or hearing the start-up jingle. An alternative handheld laser design uses a digital LCD (or LED) screen to show the power level/program for the system 10 using symbols, numbers, or letters.

Once the user completes step 102, the user then completes step 103 by holding the laser as shown in FIG. 3. Then, the user completes step 104 by pressing the laser aperture 1 against their skin where the user desires laser treatment such as on the face to address facial wrinkles or acne. Once the laser aperture 1 is fully touching the skin, the user completes step 105 and presses the initiation button 2 to begin treatment on the spot where the laser is currently positioned.

At this point, the controller of the system control board 9 begins the selected program of step 102. Step 106 is initiated by the program to determine if all safety sensors 8 are engaged with the skin. If any of the safety sensors 8 are not engaged with the skin, the system 10 controls will not energize the laser and instead will provide a low-tone audio sound representing that the system 10 is not firing due to lack of full engagement of all safety sensors 8 with the skin. After sounding the low-tone audio sound, the program will move back to step 104, which allows the user to reposition the laser system 10 and move onto step 105.

At step 106, if the safety sensor 8 is fully engaged on the skin, the controller of the control board 9 will begin firing the light emitting device 7 in step 107 according to the pre-programmed power level selected in step 102. During the firing of the light emitting device in step 107, the controller of the control board 9 will continually poll the safety sensor 8 in step 108 to ensure it is fully engaged against the skin. If step 108 shows the safety sensor 8 continues to be fully engaged, it will then determine if the program is done step 109 based on the pre-programmed timers and pulsing program. If the program is not done in step 109, it will cycle back to step 107 and continues the treatment program. If the safety sensor 8 in step 108 is ever determined to be not fully engaged with the skin, then the system 10 controls will immediately stop providing energy to the light emitting device 7 and will move to step 110.

If step 109 determines the program is complete, then the controller of the control board 9 will immediately stop providing energy to the light emitting device 7 and move to step 110. At step 110, the system 10 control will make an audio sound through the speaker or buzzer on the control board 9 to signal to the user that the treatment sequence is complete. In step 111, the system controller then wait for the safety sensor 8 to be disengaged from the skin. This step requires the user to disengage the system's safety sensors 8 from the skin before the program will end in step 112. The sequence of step 111 and step 112 requires the user to remove the device 23 from the skin before the program will end and allow the user to resume use of the system 10. This provides safety to the user so that the user does not treat the same skin repeatedly, such as by mistake, by simply pressing the initiation button 2 multiple times without first moving the system 10 off the skin.

Step 112 ends the treatment program while keeping the power on and maintaining the current program setting. At this time, the user will move the laser into the next position in step 104 and continue treating their skin until all desired skin is treated at the selected power level. If the user feels the onset of pain in certain areas of their skin, such as directly under the eyes where skin is most sensitive, they can move back to step 102 to select the correct power level for the skin being treated and then proceed through the process flow accordingly. If the user feels the that power is not sufficiently high in certain areas of their skin, such as on the forehead where skin is less sensitive, they can move back to step 102 to select the correct power level for the skin being treated and then proceed through the process flow accordingly.

During step 105, the system controller will make an audio sound to inform the user that the treatment has started successfully. The audio start-treatment sound of steps 105 and the audio stop-treatment sound of step 110 provides the user with a clear indication of when the laser starts and when it stops during full programmed operations with the safety sensors engaged correctly. The user can use these audio prompts to better acclimate themselves with the system, which facilitates moving the system 10 from spot to spot around the skin of their face in a systematic and paced manner, in one example.

An alternative programming of the system controller omits step 105 and allows the system to initiate step 107 as soon as step 106 is fulfilled. This method increases the speed of overall treatment because the user no longer needs to trigger the initiation button 2 with each treatment cycle. While this approach is considered more efficient, the prior method is considered safer as it requires direct user initiation each time the system is triggered.

Once the user is completely done treating the skin, they can allow the system to shut down automatically, as the system is programmed to time-out within a short time of no buttons being pressed (which is typically about 2 minutes). Alternatively, the user holds power button 4 for more than about 1 second and the system 10 will fully power down. When the system 10 powers down, it plays a lower-tone jingle as compared to the start-up tone, and all the LEDs 3 turn off.

To charge the battery on the device 23, the user plugs a wall charger, computer charger, or car charger to a power source. Then, the user plugs the system power end into the handheld system 10. LEDs 3 on the system 10 will flash until the battery is fully charged, then an audio sound will play and the LEDs 3 will turn off when the system 10 is fully charged. An alternative power-down sequence omits the audio portion so as not to disturb the user. The power cord to charge the system 10 may be configured to have a micro-USB end and a computer USB other end for powering by computer USB interface.

In additional examples, the system 10 can includes an additional jack or interface that accepts a computer USB plug input, and can includes wall-plug electrical outputs for plugging into a wall-plug outlet for charging. When the system 10 is charging, LED lights preferably indicate the level of battery charging completed or the amount of time left to complete charging.

Each time the system 10 is powered up by pressing button 4, the LEDs 3 typically briefly display a number of lights that indicate the amount of charge left in the battery.

The port 5 of FIGS. 1 and 2 is used to charge the system battery and connect the system 10 to another device. By connecting the system 10 to another device such as a personal computer, the system 10 can updates its firmware program, download usage data, or customize user preferences. In one example, the port 5 is a USB connection or similar interface which can auto-negotiate a connection with outside device(s).

Using this connection, the controller of the control board 9 in the system 10 can automatically execute programs to update its system program or upload data, and/or initiate a program that allows users to interface with the system's program via an external device such as a personal computer. Through this connection to a defined program, the system 10 can upload usage data which such program or external website can analyze, graph and/or provide other feedback to the user. Such feedback can advise the user on how to improve usage of the device. Through this connection, a defined program can allow the user to customize the program settings or power levels to better match the user's needs. Through this connection, a defined program could allow users to modify the audio and LED prompts to more desirable or preferred settings.

An alternate battery charging method may be used whereby electrical connections from the system 10 connect with a base-station when the system 10 is not in use. The base-station is connected to electrical power and may automatically charge the system 10 once the system is placed into the base station. The base-station may charge the system 10 through inductive charging or via direct electrical connection charging current.

The flow chart illustration of FIG. 6 shows an open-loop control of temperature based on pre-programmed settings and user definitions of the power/program setting according to their comfort level. Using this open-loop control, there is no direct temperature measurement of the epidermis 27 or dermis 28 during operation of the system 10. An alternate method of treatment is to add a temperature measurement device to measure temperature at or near the treatment area that can correlate to the epidermis 27 or dermal temperature of interest during the treatment of the skin and adjust one or more of the program attributes (laser power, pulse width, time delay between pulses, or total number of pulses) to maintain a desired temperature.

In accordance with aspects of the present invention, there is provided an improved method employing a laser apparatus. This laser apparatus emits pulse groups having pulses that deposit energy into the tissue in precisely metered formats that raise the local temperature at a treatment site in the skin to a desired level. Then, this laser apparatus maintain that desired temperature level for a selected period.

This method provides localized heating of target spots on the skin of a patient by the application of optical laser energy to the spot. The controller of the control board 9 provides for the delivery of optical laser energy to the target spot of skin in the form of a group of pulses, using a combination of pulsed beam parameters selected from laser power, pulse width, time delay between pulses, and total number of pulses. Delivery of this energy to a target spot in the affected skin causes initial heating so that the temperature of the target spot rises quickly to a desired first temperature range. Next, the temperature in the skin is maintained within a selected temperature maintenance temperature range by controlling, in the pulses, at least one of these system attributes laser power (also referred to as pulse intensity), pulse width, time delay between pulses, and total number of pulses.

The maintained temperature of the method is preferably greater than about 39 degrees Celsius. Preferably, the maintained temperature is greater than about 39 degrees Celsius and less than about 45 degrees Celsius. Experimentation has shown that less one or two degrees C. below 39 degrees C. provide less than optimal results, and two or more degrees beyond 45 degrees C. increases pain in the patient without improving the efficacy of the treatment.

A method is provided for treating skin of a human patient using a laser apparatus capable of producing an emission of laser energy in the form of a group of pulses having defined parameters. Using an optical delivery system for transmitting the defined pulse group of pulses of laser light energy, as shown in FIGS. 7-15, to the same spot on the skin of the patient. This enables the temperature or energy level to rise quickly to a desired level in the specified layer of the skin based on the laser wavelength absorption physics. Once the desired temperature is anticipated to be reached, the pulse parameters are pre-programmed to change to maintain this desired temperature or energy level for a period of time.

Figure 8:
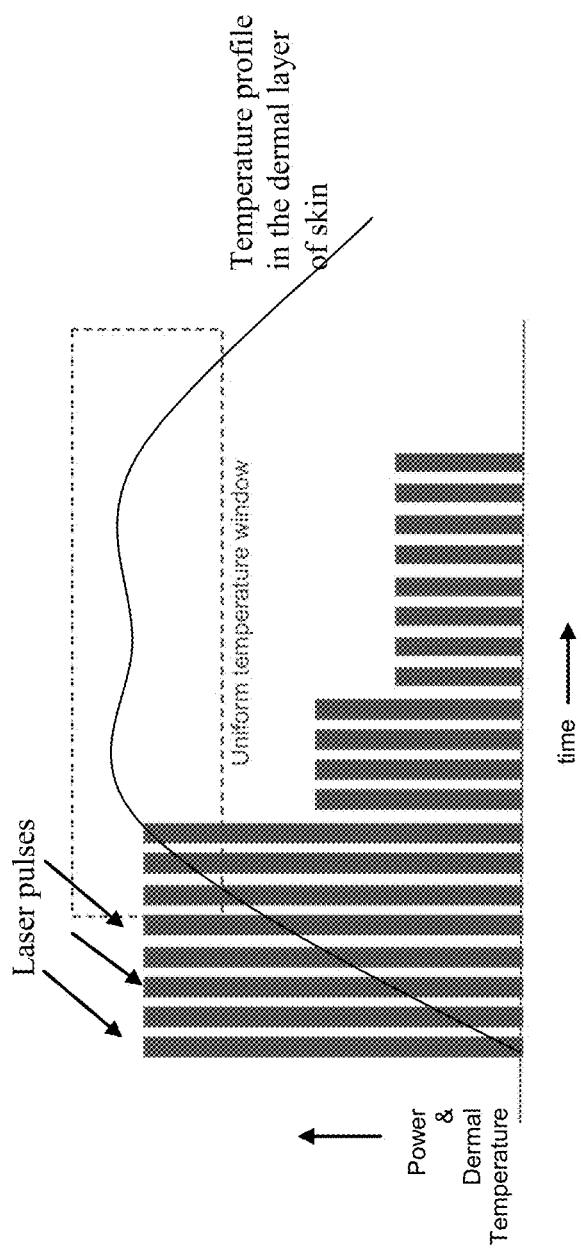
FIG. 8 is a graphical view showing a dermal temperature profile as being maintained in a narrow window of dermal temperature by reductions in applied laser power.
Figure 9:
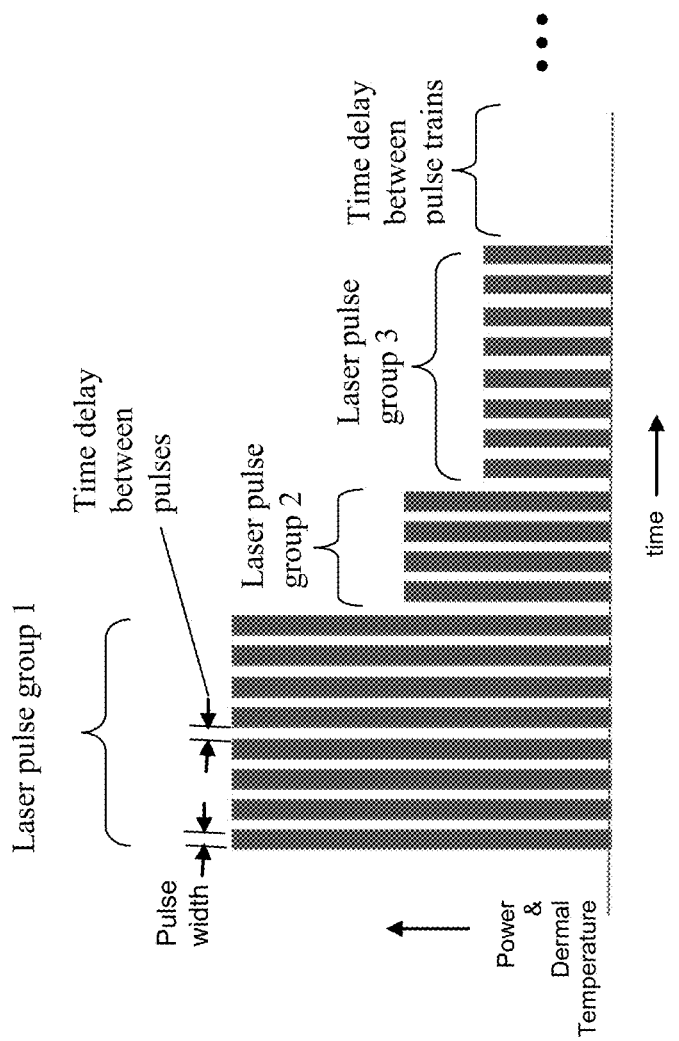
FIG. 9 is a graphical view defining additional features of FIG. 8.

More specifically, as shown in FIGS. 8 and 9, the pulsed group power generated under the control of the controller of the control board 9 is not constant and typically starts out at a high power level and long pulse duration until the desired temperature is reached. At this point, one or more of the pulse attributes or parameters (pulse power/laser current, pulse width, and time delay between pulses) is changed by the controller of the control board 9 to lower the amount of power applied into the skin from that point forward so as to maintain the temperature at a relatively constant level. In FIGS. 8 and 9, the laser power level is decreased once the desired temperature is reached or anticipated to be reached by the controller of the control board 9. The transition from initially driving high levels of energy (optical fluence) into the skin to maintaining the skin temperature can occur in many steps or configurations, utilizing different combinations of pulse attributes/parameters to attain the identical and desired outcome. In FIGS. 8 and 9, the laser power level is decreased by the controller of the control board 9 in two steps using a total of 3 power levels to achieve the desired temperature profile. Alternate methods may reduce the power in 4 or more steps, or as few as two steps, in examples.

FIGS. 8-15 show examples of modifying one or more system parameters in a non-linear way to achieve an expected desired temperature profile that raises temperature quickly in the desired tissue, then maintains the expected desired temperature once it is reached. In general, the overall energy provided to the skin is typically between 1.5 and 5.0 joules per centimeter squared.

The examples shown in FIGS. 8 & 9 changes the laser energy output by varying the power level per pulse and the number of pulses at each power level. This is accomplished by having a steady stream of pulses of high power, which can be followed by pulses of medium power, and then pulses of lower power. All of these pulses have the same time delay between them and the same pulse width. In this example, the high power pulses drive the skin temperature quickly to the expected desired level then the medium power tapers off the increase of the temperature rise such that it does not overshoot the desired level. The lower power level provides enough energy to maintain the desired temperature in the skin. These patterns are typically predetermined for particular skin conditions, skin types, and lasers, and stored in a control device such as a computer.

Figure 10:
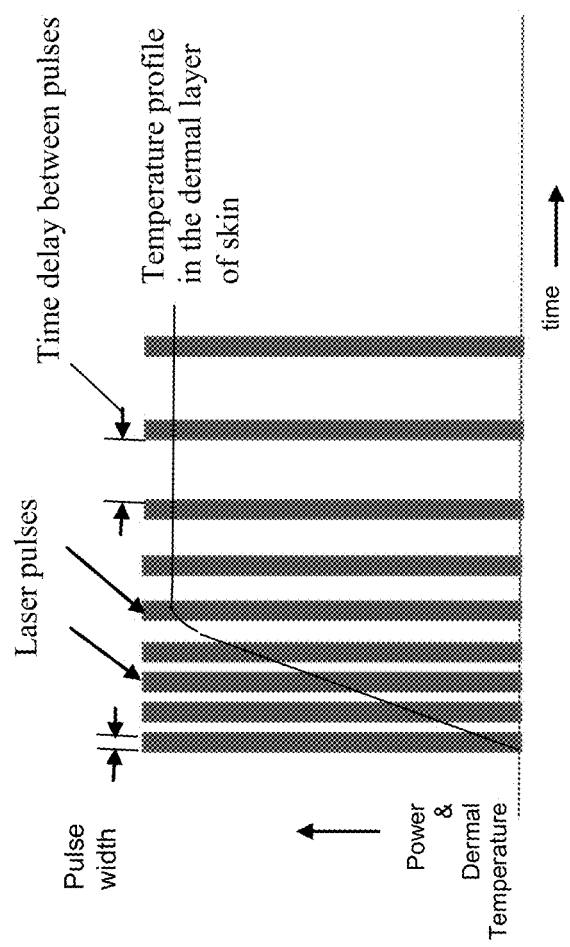
FIG. 10 is a graphical view showing a pulse pattern in which pulses are constant in pulse intensity, pulse width and change in intervals between pulses, providing a fixed temperature profile in the dermis.

An alternate way to control the laser energy output is to vary the time delay between pulses. This is accomplished by having a steady stream of pulses with small time delays between pulses followed by pulses of medium time delay between pulses and 3 pulses of longer delays between pulses. All the pulses having the same power level and the same pulse width as shown in FIG. 10. In this example, the pulses with small time delays between pulses drive the skin temperature quickly to the desired level then the pulses with medium time delays between pulses taper off the increase of the temperature rise such that it does not overshoot the desired level. The pulses with long time delays between pulses provide enough energy to maintain the desired temperature in the skin.

Figure 11:
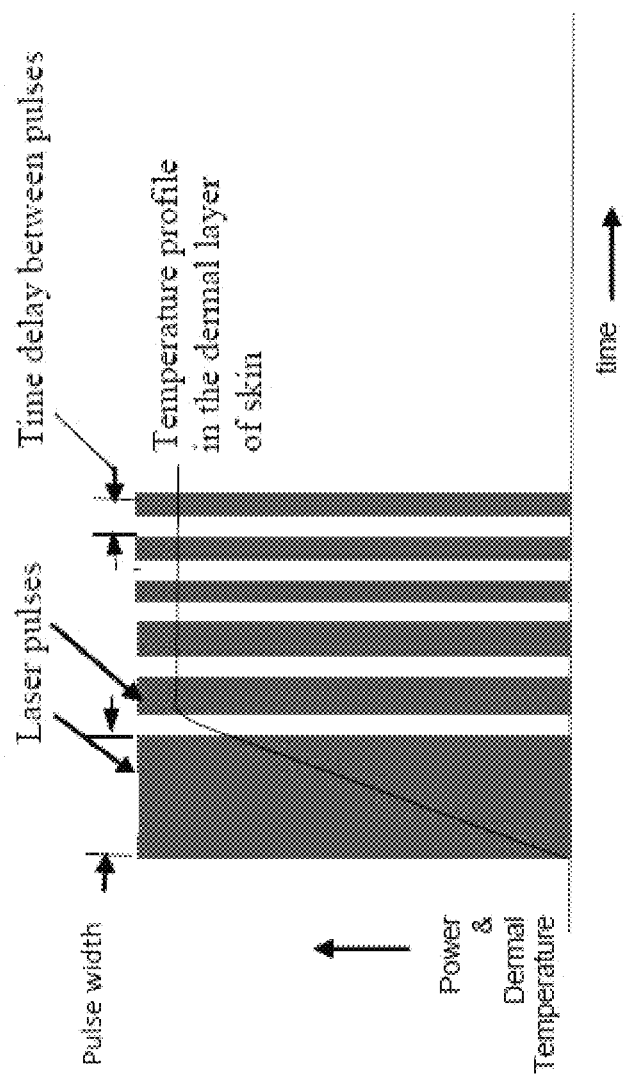
FIG. 11 is a graphical view showing a pulse pattern in which pulses change in pulse width with the same interval between pulses, pulse intensity, providing a fixed temperature profile in the dermis.

Another way to control the laser energy output is for the controller of the control board 9 to vary the pulse width of subsequent pulses, such as having long pulses followed by pulses of medium pulse width and pulses of shorter pulse width. All the pulses have the same power level and the same time delay between pulses as shown in FIG. 11. In this example, the pulses with long pulse widths drive the skin temperature quickly to the expected desired level then the pulses with medium pulse widths tapers off the increase of the temperature rise such that it does not overshoot the desired level. The short pulse width pulses provide enough energy to maintain the desired temperature in the skin.

Figure 12:
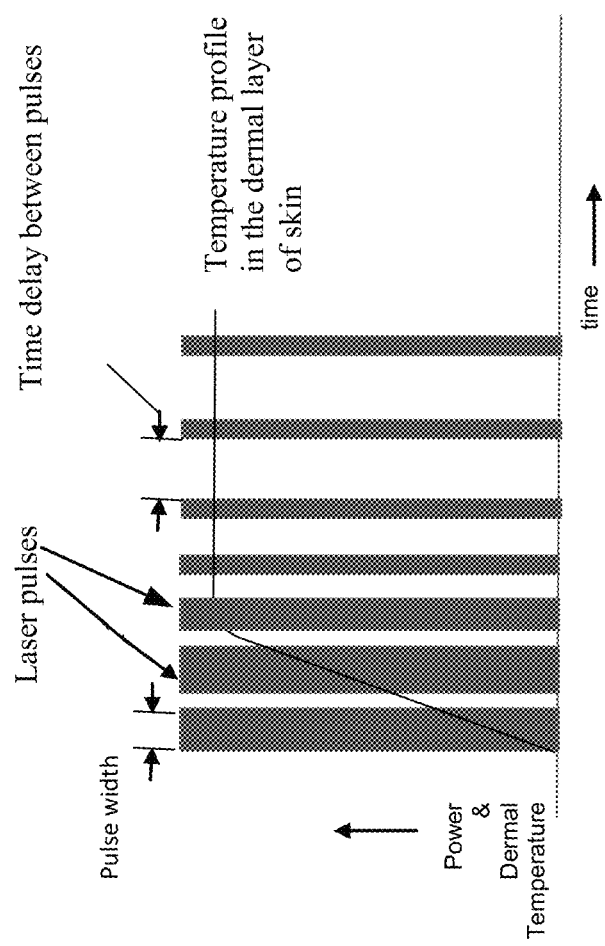
FIG. 12 is a graphical view showing a pulse pattern in which pulses change in pulse width and change in intervals between pulses with fixed pulse intensity, giving a fixed temperature profile in the dermis.
Figure 13:
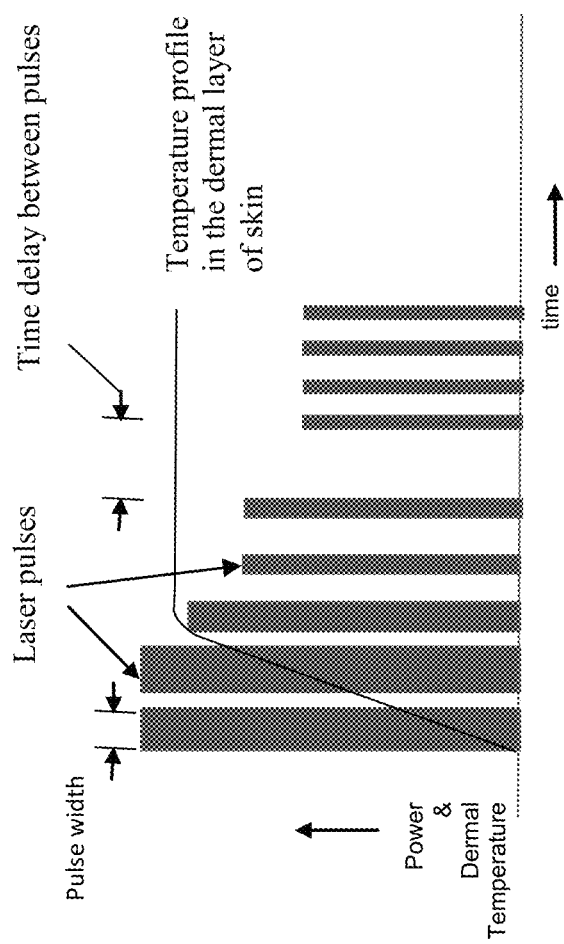
FIG. 13 is a graphical view showing a change in pulse width, pulse height (intensity), and time interval between pulses.

Another way to control the laser energy output is to vary multiple pulse settings at the same time. For example, the pulse width and time delay between pulses is varied as shown in FIG. 12. Alternatively, the pulse width, the time delay between pulses, and the power level of the pulses are all varied as shown in FIG. 13.

Another way to control the laser energy output is to provide high initial energy pulses to raise the temperature as quickly as possible, and then follow with a lower power level of pulses to allow the initial energy of the high level pulses to dissipate into the skin and achieve a uniform expected desired temperature level of this skin. This is then followed by medium-level power pulses to maintain the desired temperature level within the skin.

Figure 14:
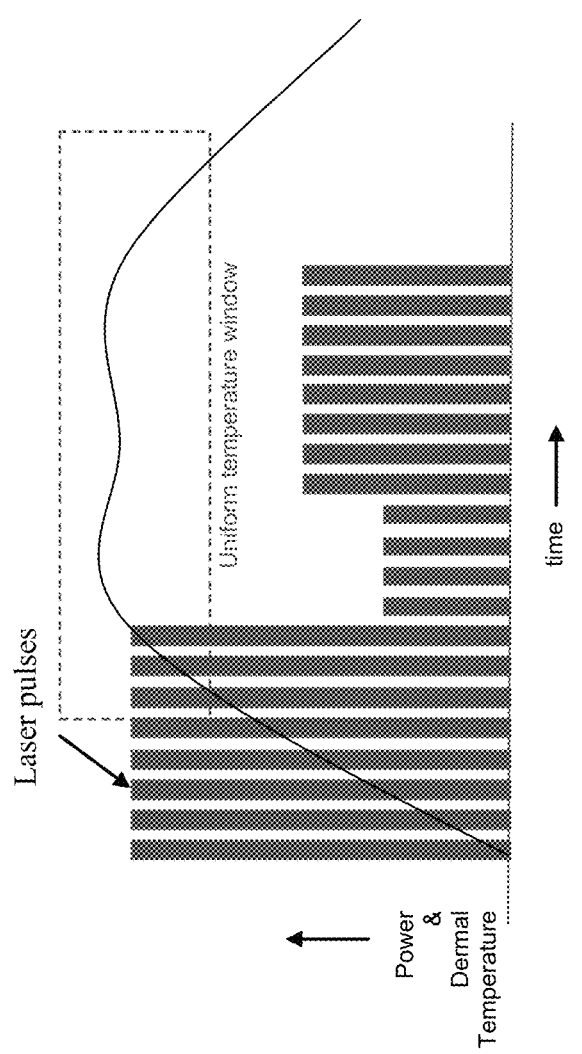
FIG. 14 is a graphical view showing a pattern of constant pulse widths, a low pulse height segment after a desired temperature is close to being achieved, followed by a higher pulse height to maintain temperature in the skin.

For example, FIG. 14 shows high intensity pulses followed by lower-level intensity pulses followed by medium level intensity pulses which drive the skin temperature to an expected given level and maintain that level in a relatively flat and constant level for a period of time. This method of the controller of the control board 9 can also be performed using similar pulse widths and time intervals between pulses. Instead of using laser power intensity, the same transition of energy from high to lower (to allow dissipation) to medium (for temperature maintenance) can be achieved by varying pulse width (long to short to medium), or time delay between pulses (short to long to medium), or a combination of any or all of these.

Figure 15:
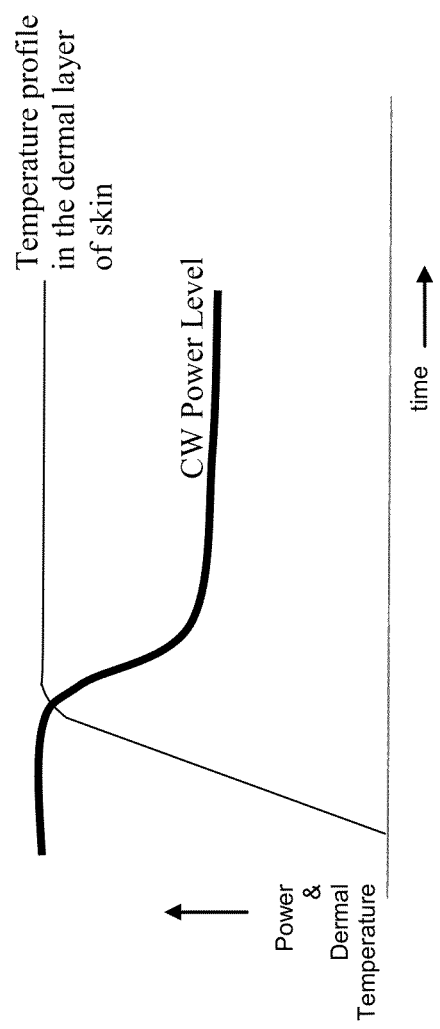
FIG. 15 is a graphical view showing the use of continuous laser energy with an initially high intensity decreasing to a lower intensity level when the desired temperature has been attained in the tissue.
Figure 16:
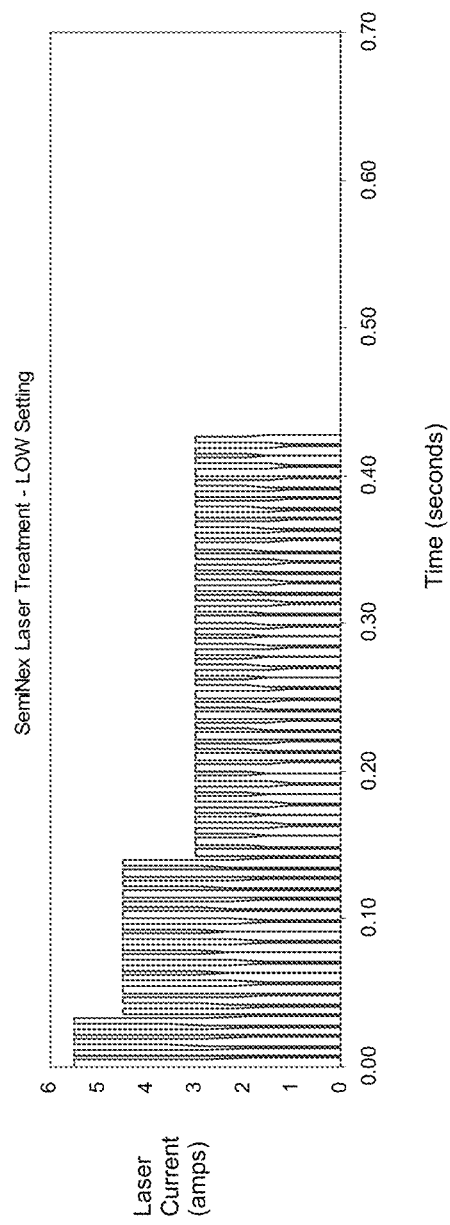
FIG. 16 is a graph of laser current versus time for the laser system at a low setting, utilizing high power pulses followed by medium power pulses followed by low power pulses.
Figure 17:
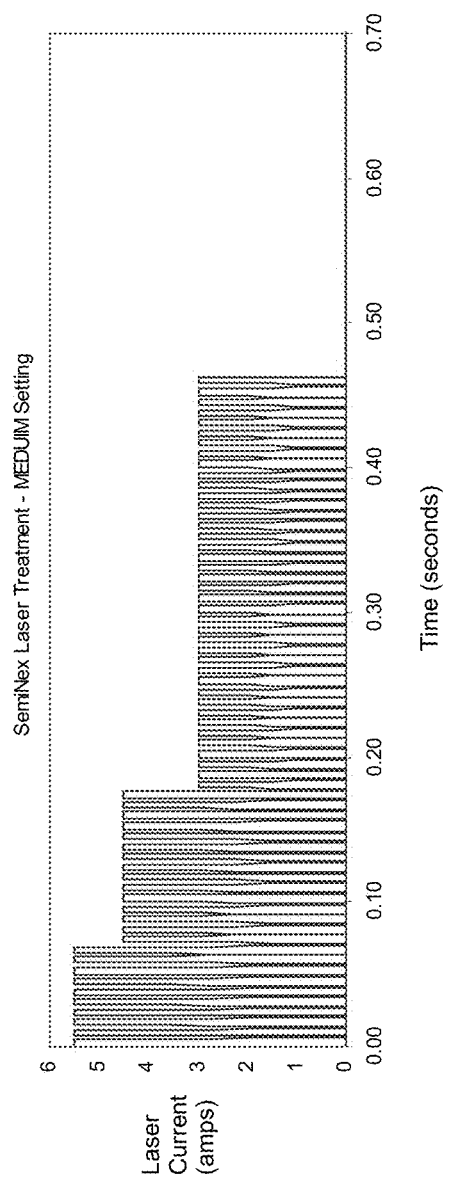
FIG. 17 is a graph of laser current versus time for the laser system at a medium setting, utilizing high power pulses followed by medium power pulses followed by low power pulses.
Figure 18:
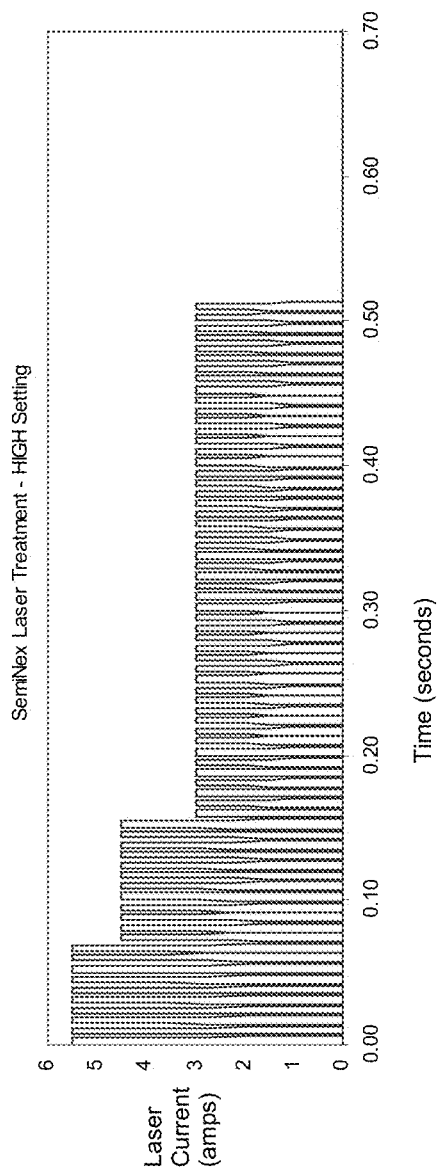
FIG. 18 is a graph of laser current versus time for the laser system at a high setting, utilizing high power pulses followed by medium power pulses followed by low power pulses.

Another way to transition the laser energy output is to vary the power setting (laser output intensity in Watts) in constant-wave form (i.e., the laser diode is always on during the treatment cycle). For example, the laser intensity can start out high, then decrease as the expected desired skin temperature is being reached as shown in FIG. 15.

In any of the preceding examples (FIG. 8-14), the number of pulses within each laser pulse grouping can be varied and the number of groupings may be varied of the controller of the control board 9 to further refine the control of the energy into the skin and desired temperature outcome within the skin. For example, instead of 3 transition steps there may be 2, 4, 5, 6, or more than 6, in examples.

In any of the above approaches, a temperature measurement feedback device can be deployed in the system to measure temperature during the treatment cycle. This temperature measurement is used to change one or more of the laser parameters (including laser power or intensity, pulse width, and time delay between pulses) to reach the desired temperature level and maintain this temperature level relatively constant for a period of time. This is often referred to as "closed-loop" controlling of the system. The prior descriptions of the system without a direct temperature measurement are often considered "open-loop" systems as they have no direct feedback on the actual outcome during treatment.

Tables 1 2, 3, and 4 herein below, and FIGS. 16, 17, 18, and 19 describe operative examples of the system 10 that are controlled by the controller of the control board 9.

In one example, a single laser system 10 was programmed with 3 power levels to represent low, medium, and high treatment energies. As shown in Table 1 and FIG. 16, the low setting has the fewest pulses of high power pulses of 5.5 Amps (2.55 Watts of optical laser power). As shown in Table 2 and FIG. 17, the medium setting has more pulses in the high setting and is otherwise identical to the low setting. Thus, the medium setting reaches a slightly higher temperature level before leveling off. Table 3 and FIG. 18 describe the high setting which is similar to the medium setting except that it has many more pulses in Group 3 to maintain the temperature for a longer period of time and thereby allow more energy into the skin without necessarily raising the temperature level within the patient, which might cause pain and discomfort for the patient.

Figure 19:
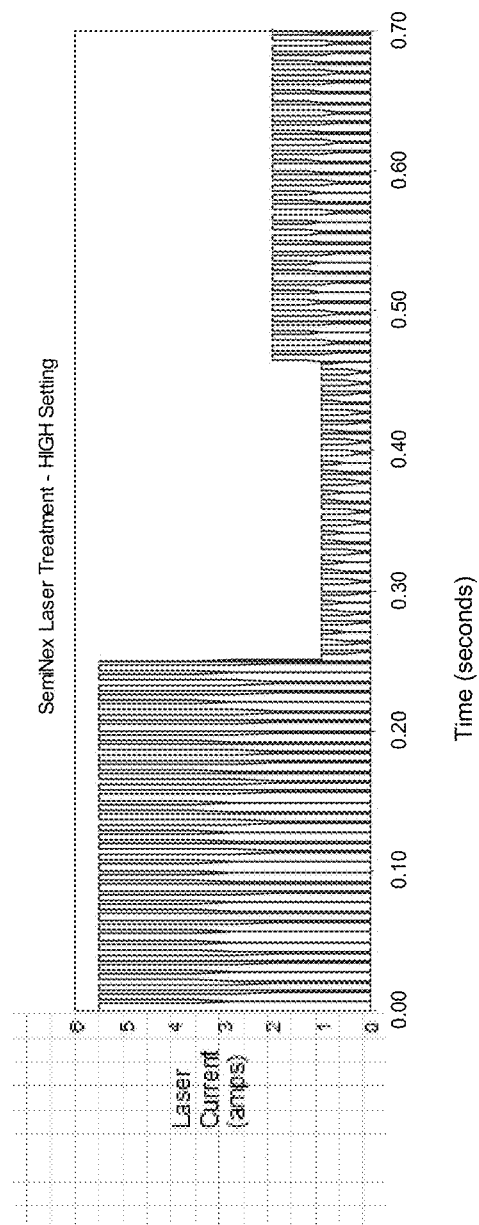
FIG. 19 is a graph of laser current versus time for the laser system at an alternate high setting, utilizing high power pulses followed by low power pulses followed by medium power pulses.

Table 4 and FIG. 19 represent the method of high power pulses followed by low power pulses followed by medium power pulses. This method allows for a high power level causing a fast temperature rise to the targeted temperature followed by the lower power level which allows for the temperature to diffuse without crossing the pain threshold followed by the medium power level which allows for the temperature to be maintained at a desired level. This example characterized by table 4 and FIG. 19 represents a method for a high power setting which emits 3.0 joules per square centimeter and could be complimented by similar pulse train which emits approximately 2.8 joules per square centimeters for medium and another pulse train which emits about 2.5 joules per square centimeter for the low power setting.

Table 1 directs 3.1 Joules into a 4 millimeter (mm)×4 millimeter (mm) spot size with the following parameters:

|  | Group 1 | Group 2 | Group 3 |  |
| --- | --- | --- | --- | --- |
| Laser Current | 5.5 | 4.5 | 3.0 | Amps |
| Laser Power | 2.55 | 2.11 | 1.37 | Watts |
| Pulse Width | 5 | 5 | 5 | milliseconds |
| Duty Cycle | 70 | 70 | 70 | % |
| Pulses | 5 | 15 | 40 |  |
| Joules | 0.06 | 0.16 | 0.27 |  |
| J/cm2 | 0.40 | 0.99 | 1.71 |  |
| Total Joules |  |  | 0.50 |  |
| Total J/cm2 |  |  | 3.10 |  |

Table 2 directs 3.5 Joules into a 4 mm×4 mm spot size with the following parameters:

|  | Group 1 | Group 2 | Group 3 |  |
| --- | --- | --- | --- | --- |
| Laser Current | 5.5 | 4.5 | 3.0 | Amps |
| Laser Power | 2.55 | 2.11 | 1.37 | Watts |
| Pulse Width | 5 | 5 | 5 | milliseconds |
| Duty Cycle | 70 | 70 | 70 | % |
| Pulses | 10 | 15 | 40 |  |
| Joules | 0.13 | 0.16 | 0.27 |  |
| J/cm2 | 0.80 | 0.99 | 1.71 |  |
| Total Joules |  |  | 0.56 |  |
| Total J/cm2 |  |  | 3.50 |  |

Table 3 directs 3.73 Joules into a 4 mm×4 mm spot size with the following parameters:

|  | Group 1 | Group 2 | Group 3 |  |
| --- | --- | --- | --- | --- |
| Laser Current | 5.5 | 4.5 | 3.0 | Amps |
| Laser Power | 2.55 | 2.11 | 1.37 | Watts |
| Pulse Width | 5 | 5 | 5 | milliseconds |
| Duty Cycle | 70 | 70 | 70 | % |
| Pulses | 10 | 12 | 50 |  |
| Joules | 0.13 | 0.13 | 0.34 |  |
| J/cm2 | 0.80 | 0.79 | 2.14 |  |
| Total Joules |  |  | 0.60 |  |
| Total J/cm2 |  |  | 3.73 |  |

Table 4 directs 3.00 Joules into a 4 mm×4 mm spot size using a step method of high power pulses followed by low power pulses followed by medium power pulses.

|  | Group 1 | Group 2 | Group 3 |  |
| --- | --- | --- | --- | --- |
| Laser Current | 5500 | 1000 | 2000 | Amps |
| Laser Power | 1.6 | 0.141 | 0.457 | Watts |
| Pulse Width | 5 | 5 | 5 | mseconds |
| Duty Cycle | 70 | 70 | 70 | % |
| Pulses | 35 | 30 | 74 |  |
| Joules | 0.29 | 0.02 | 0.17 |  |
| J/cm2 | 1.81 | 0.13 | 1.06 |  |
| Total Joules |  |  | 0.48 |  |
| Total J/cm2 |  |  | 3.00 |  |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating a patient by providing localized heating of target spots of skin, comprising:
applying optical energy having a wavelength between 1380 nanometers (nm) and 1570 nm to the target spots of skin using a laser source located within a handheld self-contained system such that the skin is heated so that a temperature of each target spot rises to a desired temperature range of greater than 39 degrees Celsius and less than 45 degrees Celsius; and
maintaining the temperature in the target spots with the handheld system within the desired heating temperature range by controlling, in pulses, at least one pulsed beam parameter being pulse energy intensity, pulse width, or a time delay between pulses, wherein one or more of the pulsed beam parameters change during the application of the optical energy, wherein the optical energy is applied for a 0.2 to 1.5 second treatment time, and wherein the total energy deposited in the skin is between 1.5 and 5.0 Joules per centimeter squared and the energy penetrates to a depth between 100 microns and 800 microns.

2. The method of claim 1, wherein the one or more pulsed beam parameters are initially set to raise the temperature in the skin, then as the heating progresses the beam parameters are changed so as to maintain the desired temperature range in the skin.

3. The method of claim 2, wherein the pulses are applied in a first group of pulses to quickly heat the skin to a target temperature, and thereafter the pulses are applied in a second group of pulses to decrease a rate of temperature increase in the target, followed by a third group of pulses to maintain the temperature of the target for a defined period.

4. The method of claim 3, wherein the second group of pulses provides less energy/time than the first group of pulses and the second group of pulses provides greater energy/time than the third group of pulses.

5. The method of claim 2, wherein an interval between pulses increases over time to maintain a tissue temperature in the desired heating temperature range during treatment.

6. The method of claim 2, wherein the pulses are of variable width and the width of the pulses decreases over time to maintain a tissue temperature in the desired heating temperature range during treatment.

7. The method of claim 2, wherein the energy intensity varies over time to maintain a tissue temperature in the desired heating temperature range during treatment.

8. The method of claim 1, wherein the energy conveyed maintains a dermal temperature of the target spots between 39 degrees Celsius and about 45 degrees Celsius for greater than about 0.5 seconds.

9. The method of claim 1, wherein a safety sensor near an aperture detects a contact or near-contact with the skin, and the method includes only emitting energy while the safety sensor continues to detect contact or near-contact with the skin.

10. The method of claim 1, wherein the laser system that performs the method is connected by a wire or through wireless communications to another device to complete one or more operations, the operations including updating device software, downloading device data, and charging device battery.

11. The method of claim 10, wherein once the laser system is connected to another device, the laser system automatically launches a program to begin data communications between the laser system and device.

12. A self-contained handheld laser system heating of target spots of skin for treating a patient, comprising:
a laser engine of the self-contained handheld laser system for generating light having a wavelength between 1380 nm and 1570 nm that is applied to the target spots of skin; and
a controller configured to drive the laser engine to generate light to maintain a temperature in the target spots within a desired heating temperature range of greater than 39 degrees Celsius and less than 45 degrees Celsius by controlling, in pulses, at least one pulsed beam parameter of the laser engine being a pulse energy intensity, pulse width, or a time delay between pulses, the controller being further configured to change one or more of the beam pulsed parameters during the application of the optical energy, wherein the optical energy is applied during a treatment time, which is 0.2 to 1.5 seconds in length, and the controller being further configured to drive the laser engine at a high fluence into the skin followed by a lower fluence within the treatment time, and wherein the total energy deposited in the skin is between 1.5 and 5.0 Joules per centimeter squared and the energy penetrates to a depth between 100 microns and 800 microns.

13. The system of claim 12, wherein the one or more pulsed beam parameters are initially set to raise the temperature in the skin, then as the heating progresses the beam parameters are changed so as to maintain the desired temperature range in the skin.

14. A method for treating a patient by providing localized heating of target spots of skin, comprising:
applying optical energy having a wavelength between 1380 nm and 1570 nm to the target spots of skin using a laser source located within a handheld self-contained system such that the skin is heated so that a temperature of each target spot rises to a desired temperature range of greater than 39 degrees Celsius and less than 45 degrees Celsius; and
maintaining the temperature in the target spots with the handheld system within the desired heating temperature range by controlling, in pulses, at least one pulsed beam parameter being a pulse energy intensity, pulse width, or a time delay between pulses, wherein one or more of the pulsed beam parameters change during the application of the optical energy, wherein the optical energy is applied for a 0.2 to 1.5 second treatment time, wherein the the total energy deposited in the skin is between 1.5 and 5.0 Joules per centimeter squared and the energy penetrates to a depth between 100 microns and 800 microns, wherein the one or more pulsed beam parameters are initially set to raise the temperature in the skin, then as the heating progresses the pulsed beam parameters are changed so as to maintain the desired temperature range in the skin with the pulses being applied in a first group of pulses to quickly heat the skin to a target temperature, and thereafter the pulses being applied in a second group of pulses to decrease a rate of temperature increase in the target, followed by a third group of pulses maintaining the temperature of the target for a remainder of the treatment time, wherein a safety sensor near an aperture detects a contact or near-contact with the skin, and wherein the system emits energy only while the safety sensor continues to detect contact or near-contact with the skin.

* * * * *